(12) United States Patent
Kulkarni et al.

(10) Patent No.: US 10,032,168 B2
(45) Date of Patent: Jul. 24, 2018

(54) SECURE VALIDATION OF FINANCIAL TRANSACTIONS

(71) Applicant: FMR LLC, Boston, MA (US)

(72) Inventors: Rajandra Laxman Kulkarni, Burlington, MA (US); Philip Peter Treleaven, Boston, MA (US); Adam Greenberg, Lincoln, MA (US); Ram Ramgopal, Andover, MA (US); Jonathan Stavis, Cohasset, MA (US); Nayan Patel, Needham, MA (US)

(73) Assignee: FMR LLC, Boston, MA (US)

( * ) Notice: Subject to any disclaimer, the term of this patent is extended or adjusted under 35 U.S.C. 154(b) by 624 days.

(21) Appl. No.: 14/642,147

(22) Filed: Mar. 9, 2015

(65) Prior Publication Data

US 2015/0254659 A1 Sep. 10, 2015
US 2017/0296710 A9 Oct. 19, 2017

Related U.S. Application Data

(60) Provisional application No. 61/949,689, filed on Mar. 7, 2014.

(51) Int. Cl.
*G06Q 20/40* (2012.01)
*A61L 31/14* (2006.01)
(Continued)

(52) U.S. Cl.
CPC .......... *G06Q 20/4016* (2013.01); *A61L 31/06* (2013.01); *A61L 31/145* (2013.01); *A61L 31/18* (2013.01); *C08G 65/00* (2013.01); *G06Q 20/325* (2013.01); *A61L 2300/44* (2013.01); *A61L 2400/06* (2013.01); *A61L 2430/20* (2013.01)

(58) Field of Classification Search
None
See application file for complete search history.

(56) References Cited

U.S. PATENT DOCUMENTS 7,275,243 B2 * 9/2007 Gibbons ................. G06F 8/61
  717/159
8,620,754 B2 * 12/2013 Fisher ................... H04W 4/21
  705/16

(Continued)

*Primary Examiner* — Steven S Kim
*Assistant Examiner* — El Mehdi Oussir
(74) *Attorney, Agent, or Firm* — Proskauer Rose LLP

(57) ABSTRACT

Methods and apparatuses, including computer program products, are described for secure validation of financial transactions. A server computing device registers a mobile device to receive notification messages from the server computing device. The server computing device transmits a notification message via a first communication channel to a notification agent executing on the registered mobile device, where the message identifies activity associated with a financial account of a user of the registered mobile device. The server computing device receives a response to the notification message via a second communication channel from an application executing on the registered mobile device, if the notification message requires a response. The server computing device stores the response in a database coupled to the server computing device, and determines whether to (i) allow, (ii) deny, or (iii) deny and report as fraud the identified activity based upon the response.

14 Claims, 6 Drawing Sheets

(51) Int. Cl.
*A61L 31/18* (2006.01)
*G06Q 20/32* (2012.01)
*C08G 65/00* (2006.01)
*A61L 31/06* (2006.01)

(56) References Cited

U.S. PATENT DOCUMENTS

| | | | | |
|---|---|---|---|---|
| 8,639,214 | B1* | 1/2014 | Fujisaki | G06Q 20/32 379/88.03 |
| 8,868,462 | B2* | 10/2014 | Nilsson | G06F 21/35 235/380 |
| 8,965,356 | B2* | 2/2015 | Miller | H04M 1/72522 455/419 |
| 9,092,803 | B2* | 7/2015 | Troiano | G06Q 30/0257 |
| 9,559,991 | B1* | 1/2017 | Wieber | H04L 51/02 |
| 9,721,243 | B2* | 8/2017 | Itwaru | G06Q 20/3227 |
| 2006/0059110 | A1* | 3/2006 | Madhok | G06Q 20/04 705/75 |
| 2007/0271149 | A1* | 11/2007 | Siegel | G06Q 30/0603 705/26.41 |
| 2009/0254440 | A1* | 10/2009 | Pharris | G06Q 20/102 705/17 |
| 2010/0312703 | A1* | 12/2010 | Kulpati | G06Q 20/32 705/44 |
| 2010/0332351 | A1* | 12/2010 | Stone | G06Q 20/102 705/27.1 |
| 2011/0251892 | A1* | 10/2011 | Laracey | G06Q 30/0253 705/14.51 |
| 2011/0258301 | A1* | 10/2011 | McCormick | H04L 67/34 709/222 |
| 2012/0157062 | A1* | 6/2012 | Kim | G06Q 30/0601 455/414.1 |
| 2012/0158590 | A1* | 6/2012 | Salonen | G06Q 10/02 705/44 |
| 2012/0240195 | A1* | 9/2012 | Weiss | H04L 63/0846 726/4 |
| 2012/0295580 | A1* | 11/2012 | Corner | H04W 12/12 455/405 |
| 2013/0024383 | A1* | 1/2013 | Kannappan | G06Q 20/40 705/71 |
| 2013/0103482 | A1* | 4/2013 | Song | G06Q 30/02 705/14.26 |
| 2013/0171981 | A1* | 7/2013 | Woo | G08O 17/02 455/420 |
| 2013/0311768 | A1* | 11/2013 | Fosmark | G06Q 20/3223 713/155 |
| 2014/0100973 | A1* | 4/2014 | Brown | G06Q 20/34 705/17 |
| 2014/0222682 | A1* | 8/2014 | Dua | G06Q 20/20 705/44 |
| 2014/0257983 | A1* | 9/2014 | Trioano | G06Q 30/02 705/14.55 |
| 2015/0120440 | A1* | 4/2015 | Jung | G06Q 20/40 705/14.51 |
| 2015/0206126 | A1* | 7/2015 | Zeinecker | H04L 63/0853 705/44 |
| 2016/0012465 | A1* | 1/2016 | Sharp | G06Q 20/18 705/14.17 |
| 2016/0277404 | A1* | 9/2016 | Chen | H04W 12/00 |
| 2016/0300237 | A1* | 10/2016 | Khan | G06Q 20/3223 |
| 2016/0342996 | A1* | 11/2016 | Navarro Luft | G06Q 20/32 |

* cited by examiner

SECURE VALIDATION OF FINANCIAL TRANSACTIONS

RELATED APPLICATIONS

This application claims priority to U.S. Provisional Patent Application No. 61/949,689, filed Mar. 7, 2014.

TECHNICAL FIELD

This application relates generally to methods and apparatuses, including computer program products, for secure validation of financial transactions.

BACKGROUND

As online banking and online financial transaction processing systems have become more prevalent, there has been a corresponding rise in hackers attempting to compromise the security of such systems to gain access to a user's account and perform fraudulent transactions. In some cases, the hacker may intercept a user's credential information and/or online session with a financial institution and proceed to execute transactions unapproved by, and in certain situations, unbeknownst to the user.

SUMMARY

Therefore, what is needed are methods and systems to notify a user regarding banking and/or other financial transactions and account activity through a secure application on the user's mobile device, and receive authorization for the activity via the secure application. The systems and methods described herein provide the advantage of securely registering the user's mobile device with the financial institution upon provisioning of the application on the device, such that the financial institution obtains specific details about the user's device which can be used to securely encrypt and authenticate transmissions—including alerts, notifications and requests for response regarding pending financial transactions—between the device and the servers of the financial institution.

The invention, in one aspect, features a method for secure validation of financial transactions. A server computing device registers a mobile device to receive notification messages from the server computing device. The server computing device transmits a notification message via a first communication channel to a notification agent executing on the registered mobile device, where the message identifies activity associated with a financial account of a user of the registered mobile device. The server computing device receives a response to the notification message via a second communication channel from an application executing on the registered mobile device, if the notification message requires a response. The server computing device stores the response in a database coupled to the server computing device. The server computing device determines whether to (i) allow, (ii) deny, or (iii) deny and report as fraud the identified activity based upon the response.

The invention, in another aspect features a system for secure validation of financial transactions. The system includes a server computing device configured to register a mobile device to receive notification messages from the server computing device. The server computing device is configured to transmit a notification message via a first communication channel to a notification agent executing on the registered mobile device, where the message identifies activity associated with a financial account of a user of the registered mobile device. The server computing device is configured to receive a response to the notification message via a second communication channel from an application executing on the registered mobile device, if the notification message requires a response. The server computing device is configured to store the response in a database coupled to the server computing device. The server computing device is configured to determine whether to (i) allow, (ii) deny, or (iii) deny and report as fraud the identified activity based upon the response.

The invention, in another aspect, features a computer program product, tangibly embodied in a non-transitory computer readable storage device, for secure validation of financial transactions. The computer program product includes instructions operable to cause a server computing device to register a mobile device to receive notification messages from the server computing device. The computer program product includes instructions operable to cause the server computing device to transmit a notification message via a first communication channel to a notification agent executing on the registered mobile device, where the message identifies activity associated with a financial account of a user of the registered mobile device. The computer program product includes instructions operable to cause the server computing device to receive a response to the notification message via a second communication channel from an application executing on the registered mobile device, if the notification message requires a response. The computer program product includes instructions operable to cause the server computing device to store the response in a database coupled to the server computing device. The computer program product includes instructions operable to cause the server computing device to determine whether to (i) allow, (ii) deny, or (iii) deny and report as fraud the identified activity based upon the response.

Any of the above aspects can include one or more of the following features. In some embodiments, the server computing device receives a request to register the mobile device from a client computing device, the request including a first set authentication credentials for a user of the client computing device. The server computing device generates a user profile record based upon the first set of authentication credentials, the user profile record including an opaque user identifier. The server computing device transmits an application to the mobile device for installation on the mobile device, and registers the mobile device using the installed application.

In some embodiments, the mobile device generates a device footprint for the mobile device and transmits the device footprint and a second set of authentication credentials received from a user of the mobile device to the server computing device. The server computing device validates the second set of authentication credentials to determine an authenticated identity of the user of the mobile device and generates a session record including an opaque session identifier and the authenticated identity of the user of the mobile device. The server computing device encrypts the opaque session identifier into a secure credential, generates an opaque token, and validates the identity of the user of the mobile device using the secure credential and the opaque token.

In some embodiments, the server computing device transmits the secure credential and the opaque token to a carrier servicing the mobile device. The server computing device transmits the secure credential, the opaque token, and carrier-specific contact information to the mobile device. The mobile device initiates a communication session with a computing device at the carrier and transmits the secure credential and the opaque token to the carrier computing device. The carrier computing device determines an identity of an owner of the mobile device based upon a call envelope associated with the communication session and transmits carrier response data comprising the secure credential, the opaque token, and the owner identity to the server computing device. The server computing device matches the owner identity with the authenticated identity of the user.

In some embodiments, if the owner identity matches the authenticated identity of the user, the server computing device generates a device record including an opaque public device identifier used to index the device record, generates an opaque private device identifier, and stores the opaque private device identifier and a phone number for the mobile device in the device record. In some embodiments, the mobile device generates an encryption key pair comprising a public key and a private key, stores the private key in an application-specific secure data store, and transmits the public key to the server computing device. The server computing device stores the public key in the user profile record, encrypts the opaque user identifier, the opaque public device identifier, and the opaque private device identifier using the public key, and transmits the encrypted opaque user identifier, the encrypted opaque public device identifier, and the encrypted opaque private device identifier to the mobile device. The mobile device stores the encrypted opaque user identifier, the encrypted opaque public device identifier, and the encrypted opaque private device identifier in the application-specific secure data store.

In some embodiments, the server computing device requests registration approval from the mobile device, receives a response to the registration approval request from the mobile device, and registers the mobile device to receive subsequent notifications based upon the response to the registration approval request. In some embodiments, the server computing device transmits an alert requesting registration approval to the notification agent of the mobile device via the first communication channel. The mobile device launches the application in response to a user action based upon the alert. The application on the mobile device transmits a request via the second communication channel to the server computing device to display a registration approval notification message, the display request including the encrypted opaque user identifier, the encrypted opaque public device identifier, and the encrypted opaque private device identifier. The server computing device validates the encrypted opaque user identifier, the encrypted opaque public device identifier, and the encrypted opaque private device identifier against the user profile record and the device record. The server computing device transmits the registration approval notification message via the first communication channel to the mobile device for display.

In some embodiments, the server computing device verifies the device footprint received from the mobile device. In some embodiments, the server computing device transmits the device footprint to a computing device of a risk management service. The risk management computing device evaluates the device footprint to generate a risk score for the footprint and transmits the risk score to the server computing device. In some embodiments, the server computing device rejects registration of the mobile device if the risk score meets or exceeds a predetermined threshold.

Other aspects and advantages of the invention will become apparent from the following detailed description, taken in conjunction with the accompanying drawings, illustrating the principles of the invention by way of example only.

BRIEF DESCRIPTION OF THE DRAWINGS

The advantages of the invention described above, together with further advantages, may be better understood by referring to the following description taken in conjunction with the accompanying drawings. The drawings are not necessarily to scale, emphasis instead generally being placed upon illustrating the principles of the invention.

DETAILED DESCRIPTION

Figure 1:
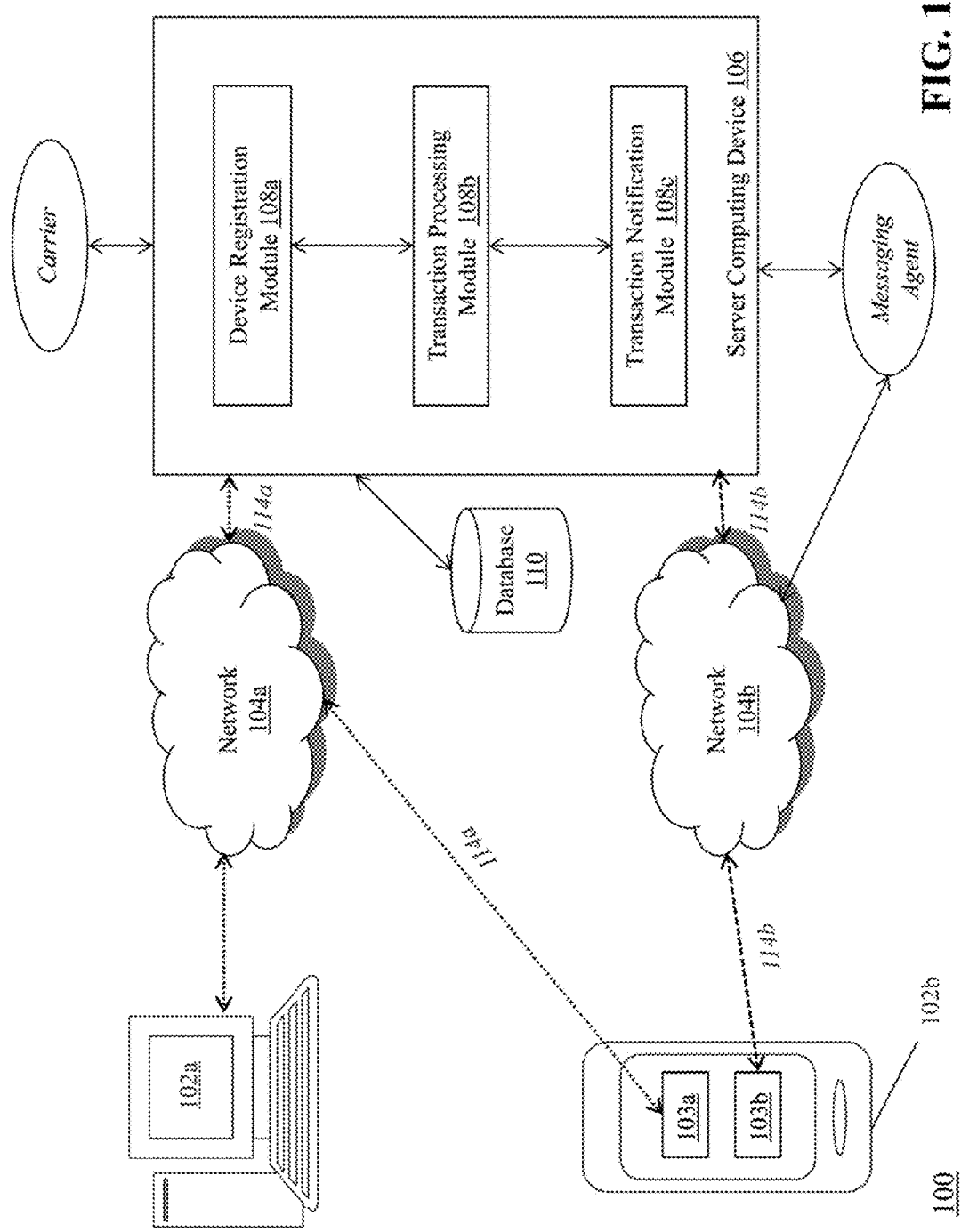
FIG. 1 is a block diagram of a system for secure validation of financial transactions.

FIG. 1 is a block diagram of a system 100 for secure validation of financial transactions. The system 100 includes a plurality of computing devices 102a-102b, an application 103a on computing device 102b, a notification agent 103b on computing device 102b, communications networks 104a and 104b, a server computing device 106 that includes a device registration module 108a, a transaction processing module 108b, and a transaction notification module 108c, and a database 110.

The plurality of computing devices 102a-102b connect to the server computing device 106 via the communications networks 104a and 104b (collectively, 104). Exemplary computing devices include desktop computers, laptop computers, tablets, mobile devices, smartphones, and internet appliances. It should be appreciated that other types of computing devices that are capable of connecting to the server computing device 106 can be used without departing from the scope of the methods and systems described herein. As shown in FIG. 1, computing device 102a is a desktop personal computer and computing device 102b is a mobile device (e.g., a smart phone). The mobile device 102b includes an application 103a located on the device and a notification agent 103b located on the device. Also, although FIG. 1 depicts two computing devices 102a-102b and one server computing device 106, it should be appreciated that the system 100 can include any number of computing devices.

The communication networks 104a-104b enable the computing devices 102a-102b to communicate with the server computing device 106 in order to conduct and authorize financial transactions. The networks 104a-104b may be local networks, such as a LAN, or wide area networks, such as the Internet and/or a cellular network. In some embodiments, the networks 104a-104b are comprised of several discrete networks and/or sub-networks (e.g., cellular Internet) that enable the computing devices 102a-102b to communicate with the server computing device 106. In some embodiments, the networks 104a-104b comprise the same physical and/or logical network.

As shown in FIG. 1, the personal computer 102a and the mobile device 102b communicate with server computing device 106 via network 104a) and the mobile device 102b also communicates with server computing device 106 via network 104b. It should be appreciated that, although the mobile device 102b may transmit communications to the server computing device 106 using the same network (in embodiments where networks 104a-104b comprise the same physical and/or logical network), the mobile device 102b uses distinct channels for its communication with the server 106. For example, the application 103a on mobile device 102b communicates with the server computing device 106 via a first channel (e.g., an internet connection) denoted by the dotted arrows 114a, while the notification agent 103b on mobile device 102b communicates with the server computing device 106 via a second channel (e.g., a phone connection) denoted by the dashed arrows 114b. It is important to distinguish the notification path (i.e., channel 114b)—the path via which the mobile device 102b receives an indication of activity related to the financial account—from the approval path (i.e., channel 114a)—the path via which the application 103a on the mobile device 102b displays the details of the activity and prompts the user to provide a disposition for the activity (i.e., allow, deny, deny and report as fraud). As will be explained in greater detail below, to maintain the integrity and security of the notification messages, the application 103a does not interact with the notification messages received by the notification agent 103b. Further, in order to act on a received notification message, the mobile device 102b requires the user to launch the application 103a—the launch should not happen automatically upon receipt of a message nor should the application 103a affect the mobile device's 102b availability to receive and display the notification message.

The server computing device 106 is a combination of hardware and software modules that enable the plurality of computing devices 102a-102b to conduct, authorize and validate financial transactions, as well as monitor such transactions (including related account activity and device activity) in order to detect potentially fraudulent actions. The server computing device 106 includes a device registration module 108a, a transaction processing module 108b, and a transaction notification module 108c. The modules 108a-108c are hardware and/or software modules that reside on the server computing device 106 to perform functions associated with conducting, authorizing, validating, and monitoring financial transaction activity. In some embodiments, the functionality of each of the modules 108a-108c is distributed among several computing devices. It should be appreciated that any number of computing devices, arranged in a variety of architectures, resources, and configurations (e.g., cluster computing, virtual computing, cloud computing) can be used without departing from the scope of the methods and systems described herein. It should also be appreciated that, in some embodiments, the functionality of the modules 108a-108c can be distributed such that any of the modules 108a-108c are capable of performing any of the functions described herein without departing from the scope of the methods and systems described herein. For example, in some embodiments, the functionality of the modules 108a-108c can be merged into a single module.

The system 100 also includes a database 110. The database 110 is coupled to the server computing device 106 and stores data used by the server computing device 106 and the modules 108a-108b to perform the functionality described above. The database 110 can be integrated with the server computing device 106 or be located on a separate computing device.

The system 100 also interacts with a carrier as shown in FIG. 1. The carrier is the service provider for the voice and data functionality of the mobile device 102b. As will be explained in greater detail below, the carrier can provide data to the system 100 for purposes of verifying the identity of a user of the mobile device 102b as well as whether the device 102b is authorized and authentic.

Figure 2:
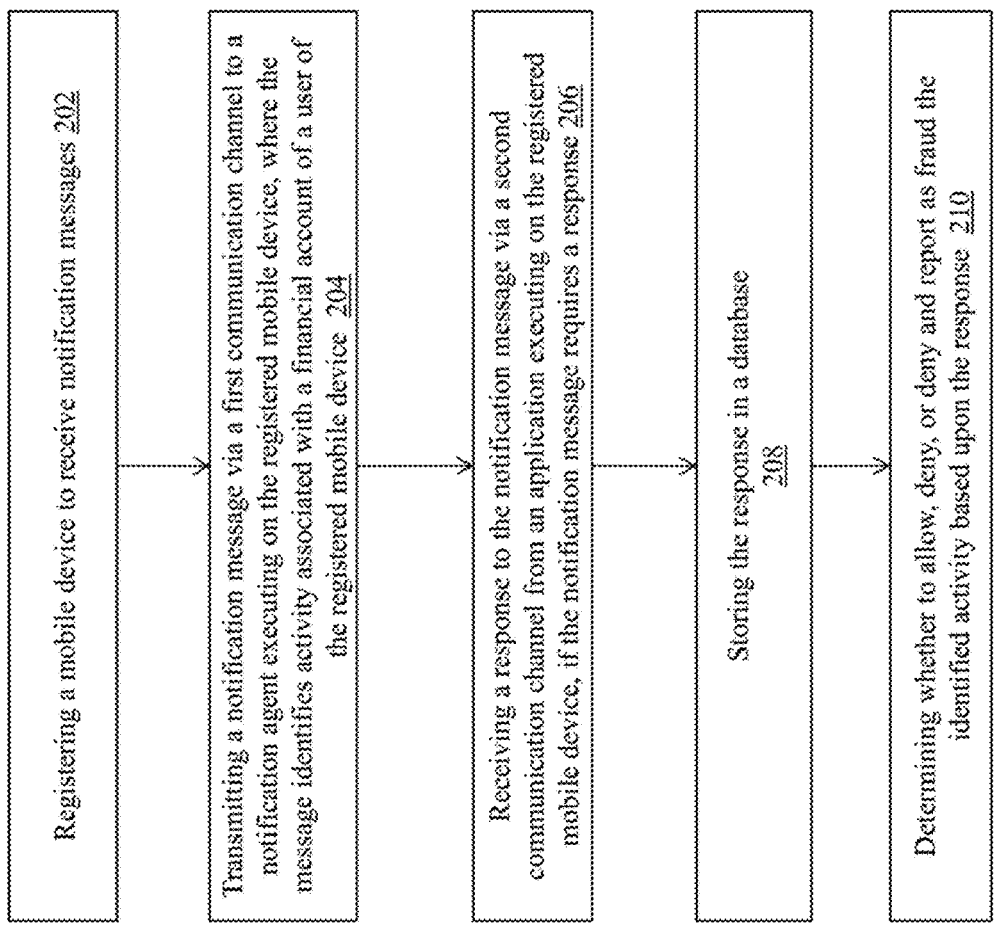
FIG. 2 is a flow diagram of a method for secure validation of financial transactions.

FIG. 2 is a flow diagram of a method 200 for secure validation of financial transactions, using the system 100 of FIG. 1. The server computing device 106 registers (202) a mobile device 102b to receive notification messages. The server computing device 106 transmits (204) a notification message via a first communication channel 114b to a notification agent 103b executing on the registered mobile device 102b, where the message identifies activity associated with a financial account of a user of the registered mobile device 102b. The server computing device 106 receives (206) a response to the notification message via a second communication channel 114a from an application 103a executing on the registered mobile device 102b, if the notification message requires a response. The server computing device 106 stores (208) the response in a database 110. The server computing device 106 determines (210) whether to allow, deny, or deny and report as fraud the identified activity based upon the response.

In one example, a user may have a financial account (e.g., a retirement account, a mutual fund account, and the like) with a financial institution, and the user may log into the institution's web site using computing device 102a to review an account and perform financial transactions, e.g., via the Internet. The user may also have a mobile device 102b for use in verifying the financial transactions performed on the institution's web site, according to the methods and systems described herein.

Figure 3:
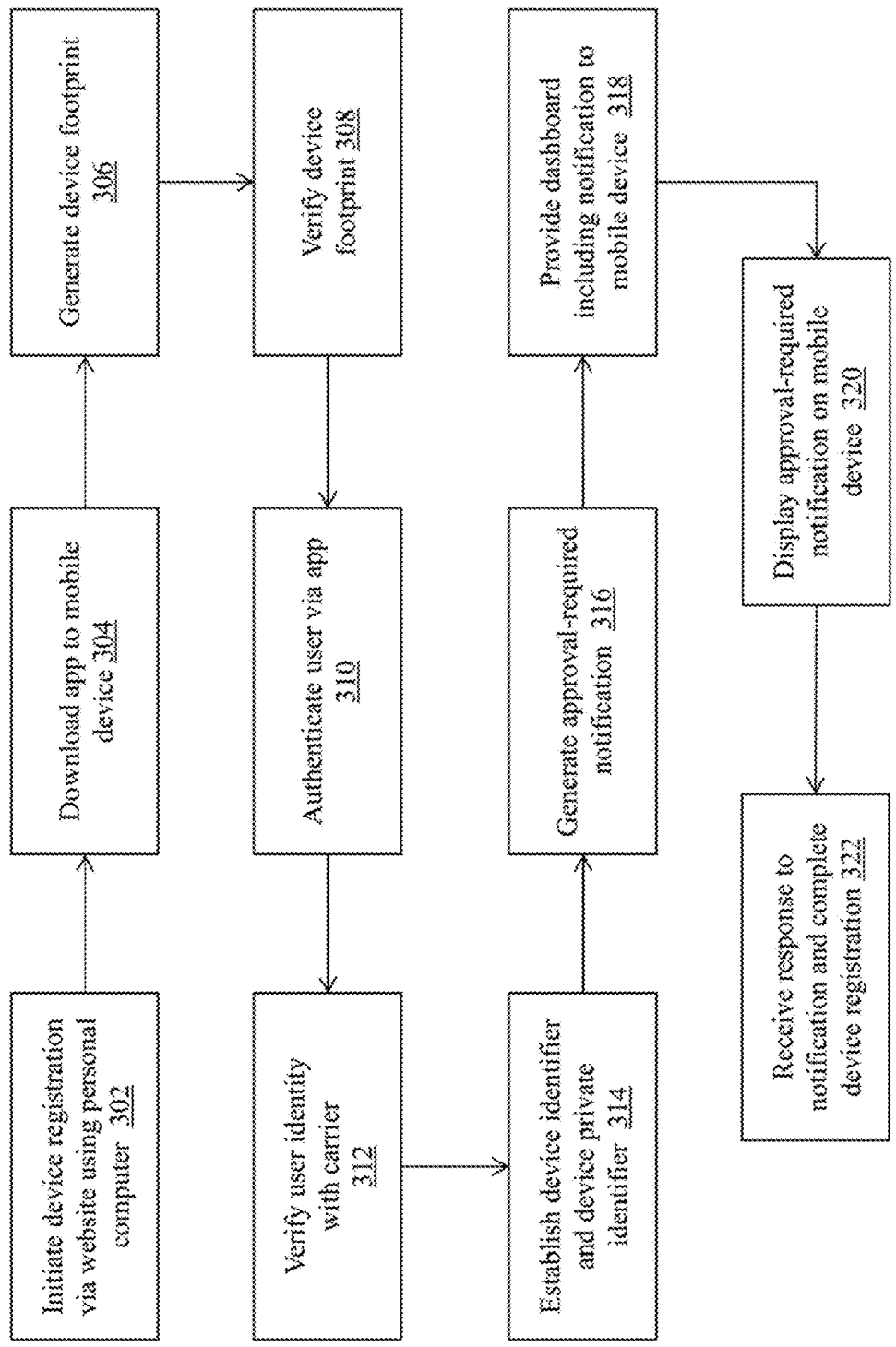
FIG. 3 is a flow diagram of a method for secure registration of a mobile computing device to be used in validating financial transactions.

In order to use the mobile device 102b for this purpose, the user first registers the mobile device 102b with the financial institution. FIG. 3 is a flow diagram of a method 300 for secure registration of a mobile computing device (e.g., mobile device 102b) to be used in validating financial transactions, using the system 100 of FIG. 1. A user at desktop computer 102a initiates (302) the device registration process by connecting to the financial institution's web site (e.g., using server computing device 106) and the user logs in by providing authentication credentials. The user selects an option (e.g., a 'register me' button) to initiate the device registration process. The device registration module 108a creates a database entry for the user (in database 110) based upon the authentication credentials and displays a dashboard which can include, but is not limited to, user identity information, activity and/or transactions for which the user may select to receive notifications on the mobile device 102b, a list of registered devices (which at this stage would be empty), and a history of notification messages and transaction dispositions (which also would be empty). The device registration module 108a also creates a unique opaque identifier, which is the public identifier that indexes the user record.

The user, via mobile device 102b, downloads (304) an application 103a (or 'app') provided by the financial institution. One example of an application is the Personal Security Command Center (PSCC) application offered by Fidelity Investments of Boston, Mass. In some examples, the user downloads the application 103a via an app store or other mechanism that is proprietary to the mobile device 102b. In some embodiments, the user has to authenticate to the app store in order to begin download of the application 103a.

Once the application 103a is downloaded and installed on the user's mobile device 102b, the user invokes the application 103a to register the mobile device. The application 103a connects to the device registration module 108a (e.g., via channel 114a). The application 103a on the mobile device 102b collects data from the device to be used in generating (306) a device footprint (i.e., a matrix or envelope of device-specific information that the device may provide as part of its normal communication process). The data to be used as part of the device footprint can include, but is not limited to, IP address, MAC address, serial number, GPS/geo-location information, telephone number, subscriber identity module (SIM) information, carrier information, and/or operating system version. It should be appreciated that other device-specific or user-specific information can be included as part of the device footprint without departing from the scope of this disclosure. The application 103a transmits the device footprint to the device registration module 108a on server computing device 106.

In some embodiments, the device registration module 108a verifies (308) the device footprint by transmitting the received device footprint to a remote verification or risk management service. The verification service evaluates the footprint and returns a risk score to the module 108a. For example, the verification service can determine whether the device footprint originated from an authentic device or whether the device has been corrupted or tampered with. If the module 108a determines that the risk score is acceptable (e.g., a low risk), the module 108a instructs the application 103a to present a login page to acquire the user's authentication credentials (e.g., username, password).

The application 103a on the mobile device 102b authenticates (310) the user by requesting that the user enter his or her authentication credentials into the login page of the application 103a, and the application 103a transmits the credentials to the device registration module 108a for validation. If the credentials are valid, the server computing device 106 creates an entry in a session database indexed by a unique opaque session identifier. The entry contains, among other things, the authenticated user identity. The server 106 encrypts the session identifier into a secure credential, and the server 106 creates a unique opaque token for display to the user via the mobile device 102b.

The server computing device 106 verifies (312) the user's identity by transmitting a request including the session identifier and the unique opaque token to the carrier associated with the mobile device 102b (as determined from the device footprint). The request indicates to the carrier that the user will be contacting the carrier (e.g., via a telephone call to a specified number) and will be providing the unique opaque token.

The server computing device 106 transmits the secure session credential, the unique opaque token, and the carrier-specific contact information (e.g., telephone number) to the mobile device 102b and instructs the user to perform an operation to contact the carrier. For example, the mobile device 102b can display a call button that, when pressed, initiates the call to the carrier.

The carrier requests the token from the user, who provides it. It should be noted that, in this embodiment, the call between the carrier and the user is a voice system phone call, not a VoIP connection. Concurrently with the call, the application 103a begins polling the server computing device 106 for the next step and also displays a page to the user that the application 103a is checking. The application 103a can also display a redial button in the event that the call fails or ends prematurely. It also should be noted that every request from the application 103a to the server computing device 106 from this point forward includes the secure session credential. The server 106 validates the secure session credential as part of the handling of each request.

The carrier obtains the call envelope (including the ANI of the caller and the number called). The carrier determines the owner of the device communications account, provides the user name, number, token value, and session identifier to the module 108a of server computing device 106, and terminates the call. In some embodiments, the carrier can provide additional information about the user (e.g., SSN, billing address) as permitted by the user. The mobile device 102a returns to the application 103a when the call terminates.

The module 108a on the server computing device 106 uses the token and the secure session identifier provided by the carrier to unite the carrier response data with the authenticated user data via the session database entry. If the data matches, the module 108a: 1) creates a device entry in the database record; 2) establishes (314) an opaque device identifier that indexes the device in the device database entry—this is the device identifier; 3) establishes a device private identifier (314) (also opaque); and 4) stores the device private identifier and the phone number in the device database entry.

The module 108a sends the application 103a a request to create an encryption key. The application 103a creates the key pair, stores the private key in the device key store (or keychain), and returns the public key to the server computing device 106. The private key does not leave the device, is not shared with other applications, and is not copied during a device replacement or repair. The server computing device 106 stores the public key in the user database record device entry, encrypts the public identifier, the device identifier, and device private identifier with the public key and sends them to the application 103a. The application 103a uses the private key to decrypt the three identifiers and stores the identifiers in the application-specific secure store on the mobile device 102b.

Concurrently, the transaction notification module 108c of the server computing device 106 generates (316) an approval-required entry in the database (e.g., notification queue) and sends an alert to the user via a messaging service appropriate to the device (e.g., iMessage, SMS, and the like). For example, the module 108c contacts the messaging agent depicted in FIG. 1 to transmit the alert to the mobile device 102b. The alert includes the device address (e.g., phone number), a notification ID, and a message instructing the user to launch the application 103a. The messaging agent delivers the alert to the notification agent 103b on the mobile device 102b. The alert indicates to the user that there is a pending notification message. In some embodiments, the mobile device 102b displays a link in the alert that opens the application 103a.

The application 103a encrypts the device private identifier with the private key and sends a request to the server computing device 106 to display the notification message. The request includes the encrypted device private identifier, the device identifier, and the public identifier. These three identifiers form the request envelope and from this point forward, appear in each request to the server computing device 106.

The server computing device 106 receives the display request, looks up the database record in database 110 using the public identifier, finds the device entry using the device identifier, checks the footprint (and in some cases, obtains a risk score from a risk management service), decrypts the device private identifier with the public key, and checks the device private identifier against the value in the database record device entry. The server computing device 106 creates an opaque session identifier that identifies the session and creates an entry indexed by this value in the session database. The entry contains the public and device identifiers and an indicator that the session is not authenticated. The server computing device 106 constructs a secure session credential that contains the session identifier (e.g., a cookie). The server computing device 106 encrypts the application 103*a* dashboard contents with the public key from the user database device entry, and provides (318) the contents and the secure session credential to the application 103*a*. The dashboard contents contains a queue of low security entries and an indicator of whether higher security entries are also pending. In some embodiments, the low security queue may contain summary entries (with no leaked privileged information) for each of the higher security queue entries.

The application 103*a* decrypts the response, saves the secure session credential for reuse during the session, and display the dashboard contents. In this case, the low security queue is empty. An option to access the higher security queue appears and indicates a single entry. The user selects the link to access the higher security queue. The application 103*a* sends the higher level queue request, the envelope, and the secure credential to the server computing device 106. In some embodiments, the low security queue can display a single summary entry for the pending higher security registration notification. The user can select this notification and the application 103*a* sends the same higher level queue request.

The server computing device 106 validates the request envelope, decrypts the secure session credential, looks up the session using the session identifier, and determines that the session is not yet authenticated. The server computing device 106 responds to the application 103*a* with a login request. The application 103*a* displays the login request. The user enters the online credentials and the application 103*a* sends the encrypted login request, the envelope, and the secure session credential to the server computing device 106.

The server computing device 106 validates the envelope and validates the authentication credentials. For example, validation requires the username and password to be correct and to map to the same authenticated identity held in the user database entry. The server computing device 106 then marks the session "authenticated," encrypts the higher level queue, and returns it to the application 103*a*.

The application 103*a* displays (320) the higher level queue on the mobile device 102*b*. In this example, the display contains only one event: the registration approval required entry and buttons for disposition of the entry, namely: approve, deny, or deny and report as fraud. In this example, the user selects the approve button. The application 103*a* sends the envelope, the secure session credential, and an encrypted request that includes the queue name, queue entry identifier, and selected disposition to the server computing device 106.

The server computing device 106 receives (322) the response, validates the envelope, determines that the session is authenticated, marks the device entry in the user database record as "registered" and clears the queue entry from the queue—opening up access to other applications to send events to the newly registered device.

The server computing device 106 then sends an alert request to the carrier. The request identifies the device phone number and includes a message that indicates that the just-approved notification was approved by the authenticated user (e.g., user name from the user database entry).

The registration process described above provides the advantage of distributing the individual pieces of information needed to conduct the binding (e.g., unique token, authentication credentials, device footprint) across a plurality of data channels (i.e., the channel between desktop computer 102*a* and server 106, the channel 114*a* between mobile device 102*b* and server 106, and the channel 114*b* between mobile device 102*b* and server 106). In some embodiments, at no point in the device registration and binding process does any channel pass all of the information required for registration. Therefore, an attacker would not be able to perform a registration and binding of his own device without having access to each of the separate secure channels described above. It should be appreciated that a user can register multiple different devices with the server computing device 106 to receive notifications and perform authorization of financial transactions.

Either before or after the registration process described above, the application 103*a* on the mobile device 102*b* provides a personalization interface for the user to customize the types of transactions for which he or she would like to receive notifications and the level of response required for each transaction. For example, a high net-worth individual that has a lot of account activity across her portfolio may not want to receive a notification for every transaction. Another user may want to receive a notification for every transaction, but only provide a response approving or denying the transaction if it exceeds a predetermined threshold value (e.g., $500). Yet another user may want to receive a notification for every transaction and provide a response along with certain authentication credentials before the transaction is processed. The methods and systems described herein allow the user to tailor his or her notifications in a flexible fashion.

The mobile device 102*b* can display a list of possible transactions and/or activity types associated with the user's account (e.g., funds deposit, funds withdrawal, trade execution, address change). In one example, the user can select (i) which transactions should not result in a notification from the server 106 to the mobile device 102*b*, (ii) which transactions should result in a notification, (iii) which transactions should result in a notification and require a response to allow/deny the transaction, and (iv) which transactions should result in a notification, require a response to allow/deny, and require the entry of a password or other authentication credential via the mobile device 102*b* at the time of response. In this way, the user can customize the level of interaction he or she has with the notification system. Once the user had defined the types of transactions and level of notification desired, the device registration module 108*a* stores the user's responses in database 110.

In some cases, the financial institution may impose limitations on the types of notifications that are required to be received by the mobile device 102*b*. For example, the institution may require that all funds transfers over a specific threshold (e.g., $10,000) initiate a notification message to the mobile device 102*b* of the user associated with the account. In other examples, there may be governmental or other legal requirements imposed on the notification system (i.e., for securities purchases that exceed 2,000 shares, the user may be required to enter authentication credentials into the application 103*a* before the trade is executed).

It should be appreciated that the user can access his or her notification preferences at any time, either via the application 103*a* on the mobile device 102*b* or via logging into the financial institution's web site and reviewing his or her notification preferences there.

Once the mobile device 102b is registered with the server computing device 106, the mobile device 102b can begin to receive notification messages associated with account activity and transactions from the transaction processing module 108b of the server 106 computing device. FIGS. 4A-4F are flow diagrams and screenshots of exemplary use cases for secure validation of sensitive transactions, using the system 100 of FIG. 1.

Figure 4A:
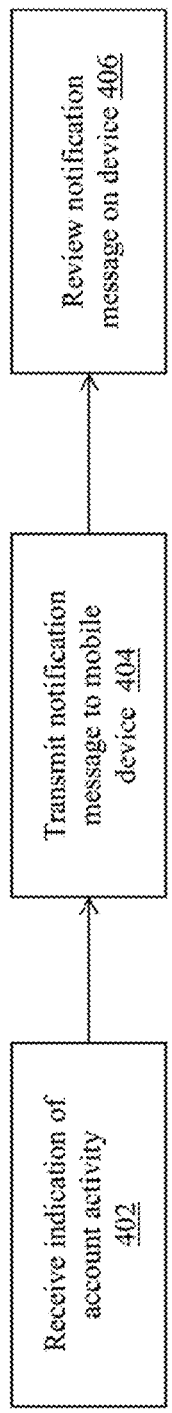
FIGS. 4A-4F are flow diagrams and screenshots of exemplary use cases for secure validation of financial transactions using a mobile computing device.
Figure 4B:
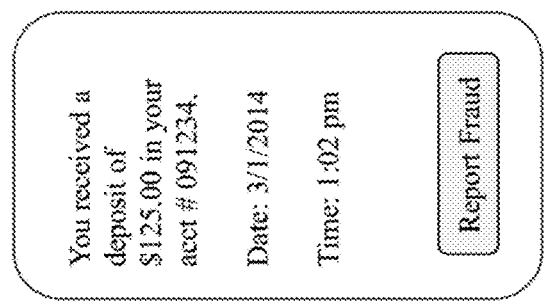

FIG. 4A depicts an exemplary use case where the mobile device 102b receives an alert message from the transaction notification module 108c. When the user launches the application 103a, the application 103a retrieves a notification message that requires no further action by the user. The transaction notification module 108c receives (402) an indication that account activity has occurred (e.g., a deposit has been made) against the user's brokerage account. The user has configured his preferences such that the application 103a on the mobile device 102b receives a notification message for this type of activity. The transaction processing module 108b transmits (404) a notification message to the application 103a on the mobile device 102b and displays pertinent information about the deposit (as shown in FIG. 4B). The user reviews the details of the transaction and no further action is required. The deposit is finalized, and the transaction processing module 108b stores a record of the notification message associated with the actual transaction in database 110.

Figure 4C:
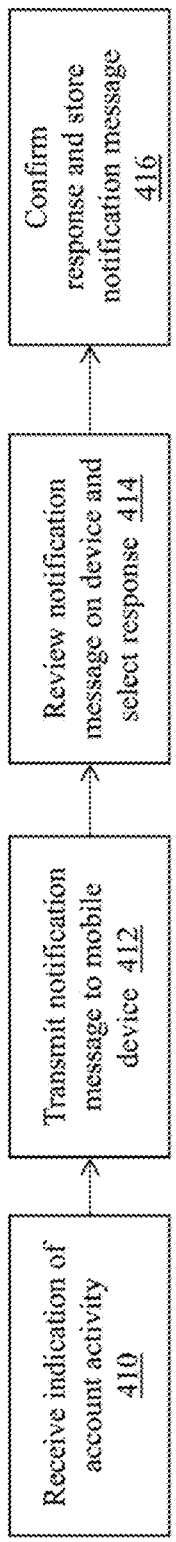
Figure 4D:
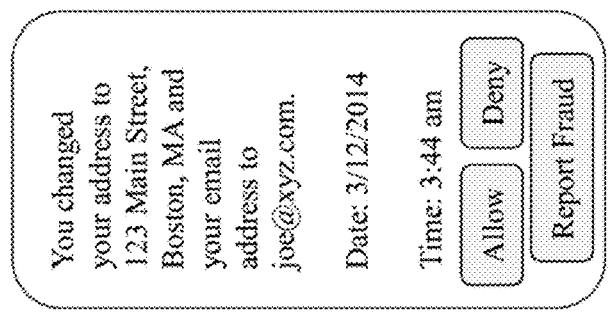

FIG. 4C depicts an exemplary use case where the mobile device 102b receives an alert message from the transaction notification module 108c. When the user launches the application 103a, the application 103a requests notification messages from the module 108c. The module 108c (perhaps after requiring user authentication) returns the notification messages to the application 103a for display to the user. One of the notification messages requires the user to provide a response to the message. The transaction notification module 108c receives (410) an indication of account activity (e.g., that the mailing address and email address associated with her investment account has changed). The user has configured her preferences such that the application 103a on the mobile device 102b receives a notification message for this type of activity. Further, the user has configured her preferences to require authorization from the mobile device 102b before finalizing the address changes. The transaction processing module 108b transmits (412) a notification message to the application 103a on the mobile device 102b which displays pertinent information about the address changes as well as an input mechanism (e.g., buttons) to allow the user to provide a response to the message (as shown in FIG. 4D). The user reviews (414) the details of the activity and selects the Allow button. The transaction processing module 108b confirms (416) that the address changes are authorized and updates the addresses (or instructs another system to perform the update). The transaction processing module 108b stores a record of the notification message associated with the address changes in database 110. The application 103a displays a confirmation message for the address changes on the mobile device 102b.

Figure 4E:
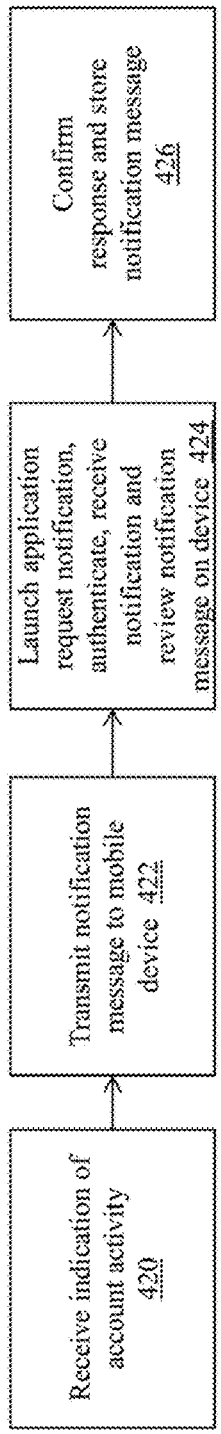
Figure 4F:
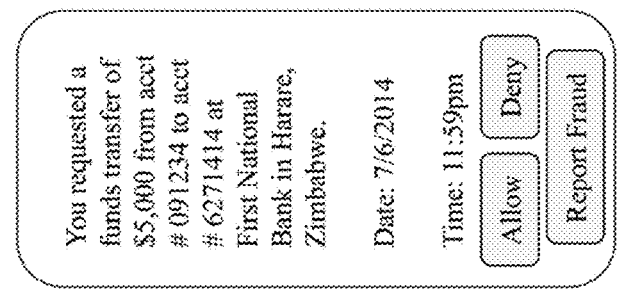

FIG. 4E depicts an exemplary use case where the mobile device 102b receives an alert message from the transaction notification module 108c. When the user launches the application 103a, the application 103a requests notification messages from the module 108c. The module 108c (perhaps after requiring user authentication) returns the notification messages to the application 103a for display to the user. One of the notification messages requires the user to provide a response to the message and provide authentication credentials to the application 103a. The transaction processing module 108b receives (420) an indication that account activity has occurred (e.g., a funds transfer has been initiated to withdraw funds from the user's savings account). The user has configured her preferences such that the application 103a on the mobile device 102b receives a notification message for this type of activity. Further, the user has configured her preferences to require log in and authorization from the application 103a on the mobile device 102b before finalizing the funds transfer. The transaction processing module 108b transmits (422) a notification message to the application 103a on the mobile device 102b and displays pertinent information about the funds transfer as well as an input mechanism to launch the application 103a on the mobile device 102b so that the user can authenticate and provide a response to the message (as shown in FIG. 4F). After the application 103a launches and the user has authenticated to the application, the user reviews (424) the details of the activity and selects the Deny button (as, for example, the receiving account may be unfamiliar to the user). The transaction processing module 108b confirms (426) that the fund transfer is not authorized and prevents the transfer from being finalized. The transaction processing module 108b stores a record of the notification message associated with the funds transfer in database 110. The application 103a displays a confirmation message for the denial of the funds transfer on the mobile device 102b. In some cases, the module 108b may require the user to enter a separate transaction password in addition to authenticating to the application 103a before the transaction can be approved. Such an implementation provides the advantage of preventing fraudulent activity where the mobile device 102b is lost or stolen while the user is already logged in to the application 103a.

As shown in the screenshots of FIGS. 4B, 4D, and 4F, the application 103a can also include a user input mechanism (e.g., a button) to enable the user to report any transaction or activity as fraudulent, when displaying the notification message on the mobile device 102b. If the user deems the transaction fraudulent and activates the button, the transaction processing module 108b receives the response and can alert other computing systems coupled to the server computing device 106 to conduct further analysis of the transaction through use of specialized fraud detection systems and to take appropriate remediation measures if necessary (such as alerting law enforcement authorities).

Detailed Use Case

The following section includes a more detailed use case regarding a money transfer using the system 100 of FIG. 1. In this use case, the user logs into the financial institution web server computing device (e.g., device 106) using browser software on a desktop or laptop computer (e.g., computer 102a) to perform a money transfer. The user specifies the account information of the recipient, the amount of money to transfer, and presses the submit button to initiate a money transfer. The server computing device 106 notifies him that execution of the money transfer requires approval via the application 103a installed on his registered mobile device 102b. A money transfer application or web service (e.g., transaction processing module 108b) on the server computing device 106, via the browser, asks him to review and approve the transaction using the application 103a.

The money transfer application on the server computing device 106 sends an event to the transaction notification module 108c notifying the module 108c that a money transfer transaction has been initiated which requires user approval. The money transfer application provides user information and money transfer details (e.g., source account, destination account, amount of transfer, and the like) to the module 108c.

The module 108c creates an approval-required entry in the database record (notification queue) and sends an alert to the user via the messaging service appropriate to the device. The alert request includes the device address (phone number), possibly a notification ID, and a message instructing the user to visit the application 103a. In this example, the messaging agent delivers the alert to the device 102b. The alert indicates to the user that there is a pending notification. The device 102b displays a link in the alert. The link opens the application 103a.

The application 103a encrypts the device private identifier with the private key and sends a request to the module 108c to display the notification message. The request includes the encrypted device private identifier, the device identifier, and the public identifier. These three identifiers form the request envelope and from this point forward, appear in each request to the server computing device 106.

The module 108c receives the display request, looks up the database record with the public identifier, finds the device entry with the device identifier, checks the footprint (and in some cases, obtains a risk score from a risk management service), decrypts the device private identifier with the public key, and checks the device private identifier against the value in the database record device entry. The module 108c creates an opaque session identifier that identifies the session and creates an entry indexed by this value in the session database. The entry contains the public and device identifiers and an indicator that the session is not authenticated. The module 108c constructs a secure session credential that contains the session identifier (e.g., a cookie). The module 108c encrypts dashboard contents with the public key from the user database device entry and returns the dashboard contents and the secure session credential to the application 103a. The dashboard contents contain the queue of low security entries and an indicator of whether higher security entries are also pending. In some embodiments, the low security queue may contain summary entries (with no leaked privileged information) for each of the higher security queue entries.

The application 103a decrypts the response, saves the secure session credential for reuse during the session and displays the dashboard contents. In addition to displaying low priority queue entries, the application 103a displays a link to access the higher security queue entries. The user selects the link to the higher security queue. The application 103a sends the higher level queue request, the envelope, and the secure credential to the module 108c.

The module 108c validates the request envelope, decrypts the secure session credential, looks up the session using the session identifier, and determines that the session is not yet authenticated. The module 108c responds to the application 103a with a login request. The application 103a displays the login request. The user enters the online credentials and the application 103a sends the encrypted login request, the envelope, and the secure session credential to the module 108c.

The module 108c validates the envelope and validates the authentication credentials. In this example, validation requires the username and password to be correct and to map to the same authenticated identity held in the user database entry. The module 108c then marks the session "authenticated", encrypts the higher level queue, and returns the higher level queue to the application.

The application 103a displays the higher level queue to the user. This display contains one or more notifications with a money transfer request with buttons for disposition, namely: approve, deny, or deny and report as fraud. The user selects approve. The application 103a sends the envelope, the secure session credential, and an encrypted request that includes the queue name, queue entry identifier, and selected disposition to the module 108c.

The module 108c validates the envelope, determines that the session is authenticated, marks the device entry in the user database record as "approved", communicates user approval to the money transfer application and clears the queue entry from the queue opening up access to other applications to send events to the registered device.

The module 108c then sends an alert request to the carrier. This request identifies the device phone number and includes a message that indicates that the just-approved notification message was approved by the authenticated user (user name from the user database entry). This concludes the money transfer approval process.

It should be appreciated that, for the exemplary use cases provided above, the transaction processing module 108b and the application 103a on the mobile device 102b communicate via a secure, encrypted communication session. The data passing between the module 108b and the application 103a in the session can be encrypted by native device/protocol encryption (e.g., SSL) in conjunction with the proprietary encryption methodology referenced above.

Also, for any of the exemplary use cases described above, the alert message does not contain any specific information about the transaction, only that some (unspecified) activity has occurred relative to the user's account(s) or information. The transaction notification module 108c can transmit a generic alert message to the mobile device 102b—e.g., "There is a transaction awaiting your review"—and prompt the user to launch the application 103a (and in some cases authenticate to the application 103a) before the transaction details are displayed. In some embodiments, the transaction notification module 108c can use existing communication protocols, such as SMS, to transmit the generic notification message to the user. In addition, the user may prefer for privacy or security reasons that subsequent notification messages retrieved via the application 103a not contain certain details regarding the underlying transaction to avoid potential disclosure by others viewing the application 103a (e.g., looking over his shoulder).

It should be appreciated that the systems and methods described above can be applied to the context of a third party (e.g., a broker, agent, spouse) performing transactions affecting an account of the user associated with the mobile device 108b. For example, the user may authorize his investment advisor to perform trades and funds transfers for his investment account. When the investment advisor performs a transaction for which the user wants to receive notification messages, the transaction processing module 108b of the server computing device 106 transmits the notification messages to the application 103a on the user's mobile device 102b as previously described. Even though the user was not the person that initiated the transaction, he still is able to be notified of the transaction and, if necessary, approve or deny the transaction in a secure fashion using the mobile device 102b.

As described above, the server computing device 106 can store detailed attributes associated with each notification message that is generated. For example, the transaction processing module 108b of the server computing device 106 can store a variety of information associated with the notification message, such as: timestamp, transaction type, response type, transaction details, device details, geo-location information, message duration, and the like. As this data store accumulates over time, the data can be analyzed for trends in transaction and notification activity for particular users or across particular business segments for the financial institution—which enables the institution to home in on potentially problematic transactions and/or improve efficiencies with respect to the notification and security processes.

Another aspect of the methods and systems described herein is the ability for a user to register multiple mobile computing devices to receive notification messages. Each mobile device (e.g., device 102b) has a unique device footprint, and the server computing device 106 generates a unique identity token for each mobile device. As a result, each mobile device is able to separately authenticate to the server computing device 106 in a secure fashion. In addition, the server computing device 106 maintains a timestamp associated with the last use of the particular mobile device. The server 106 can discard the binding/registration for any device that has a last use timestamp exceeding a predetermined expiration date (or dormant limit).

Periodically, the server computing device 106 may require the mobile device 102b to update the identity token. For example, the server 106 can transmit a notification message to the application 103a on the device 102b that the token has expired. The application 103a prompts the user for one or more authentication credentials prior to providing the new identity token.

It should be appreciated that another advantage of the methods and systems described herein is that the application 103a does not locally store the notification messages or responses to the messages on the device 102b (other than in a transitory fashion). Therefore, an attacker cannot recover any sensitive information from the mobile device 102b. In addition, in one embodiment, the only private data stored on the mobile device 102b is the identity token—which is essentially unusable by an attacker to perform fraudulent transactions without the device footprint (and in some cases, a user password or other authentication credential). Therefore, an attacker cannot simply port a copy of the application 103a to another mobile device and be able to conduct any transactions or receive notification messages.

Also, in some embodiments, the notification messages which require action on the user's part (e.g., allow, deny, authenticated allow or deny) can be valid until for a predetermined amount of time (as defined by the financial institution or, in some cases, user defined during registration). After expiration of the amount of time, the transaction may be abandoned or, in the case of time sensitive transactions such as a limit order, the transaction may be invalidated during approval due to price movement in the market. In either case, the user is notified via the application 103a regarding the abandonment of the transaction due to timeout and the invalidation.

It should also be appreciated that the methods and systems described herein support a multiple user approval model (e.g., joint account requiring approval from both partners for any transaction). The system allows multiple devices to be registered against a single account, and the system distributes notices to, and requires approvals from, multiple registered devices simultaneously for the same transaction. In addition, in some embodiments, one, some, or all registered devices can provide approvals before the transaction is considered 'approved.' For example, it may be sufficient for only three of five board members (i.e., quorum) to authorize a low value transaction, but all five would be required for high value transaction. In another example, for joint account holders it may be sufficient for one of the account owners to approve the transaction. The account holders can personalize the rules dictating the required number of approvals needed for each transaction/notification type, provided all account holders "approve" the rules. Also, in order to clearly communicate who initiated the action generating the notification, a user name or user identification is provided as part of the notification message detail.

It should also be appreciated that, in some embodiments, after an action is taken for a given notification message, the application 103a can receive notification of the action and any corresponding result (e.g., financial effect of the action) as a "notification without action." However, depending on the sensitivity of the information, the user may or may not have to authenticate to the application 103a before accessing the details of the notification message. As an example, after a user approves an address change notification message, the user may need to authenticate to access the notification of confirmation of the address change.

Also, in the case of certain transactions initiated by the financial institution on the user's account, the user is notified—however, these notification messages may not have any user action associated with them. For example, if the user has 500.6 shares of stock and sells 500 shares based on an account agreement, the financial institution may sell/buy the remaining fraction of shares (e.g., 0.6 shares) for convenience of the user. In this case, even if the user has required approval of notification for the trade event, he may be only notified about the event. However, all events executed on behalf of user will abide by the notification rules defined during the registration/notification management process.

Finally, it should be understood that while the methods and systems are described above in the context of a financial services application, the methods and systems can be adapted to other applications involving the conveyance of sensitive or privileged information and notification of same (e.g., legal, health care, human resources).

The above-described techniques can be implemented in digital and/or analog electronic circuitry, or in computer hardware, firmware, software, or in combinations of them. The implementation can be as a computer program product, i.e., a computer program tangibly embodied in a machine-readable storage device, for execution by, or to control the operation of, a data processing apparatus, e.g., a programmable processor, a computer, and/or multiple computers. A computer program can be written in any form of computer or programming language, including source code, compiled code, interpreted code and/or machine code, and the computer program can be deployed in any form, including as a stand-alone program or as a subroutine, element, or other unit suitable for use in a computing environment. A computer program can be deployed to be executed on one computer or on multiple computers at one or more sites.

Method steps can be performed by one or more processors executing a computer program to perform functions of the methods and systems described herein by operating on input data and/or generating output data. Method steps can also be performed by, and an apparatus can be implemented as, special purpose logic circuitry, e.g., a FPGA (field programmable gate array), a FPAA (field-programmable analog array), a CPLD (complex programmable logic device), a PSoC (Programmable System-on-Chip), ASIP (application-specific instruction-set processor), or an ASIC (application-specific integrated circuit), or the like. Subroutines can refer to portions of the stored computer program and/or the processor, and/or the special circuitry that implement one or more functions.

Processors suitable for the execution of a computer program include, by way of example, both general and special purpose microprocessors, and any one or more processors of any kind of digital or analog computer. Generally, a processor receives instructions and data from a read-only memory or a random access memory or both. The essential elements of a computer are a processor for executing instructions and one or more memory devices for storing instructions and/or data. Memory devices, such as a cache, can be used to temporarily store data. Memory devices can also be used for long-term data storage. Generally, a computer also includes, or is operatively coupled to receive data from or transfer data to, or both, one or more mass storage devices for storing data, e.g., magnetic, magneto-optical disks, or optical disks. A computer can also be operatively coupled to a communications network in order to receive instructions and/or data from the network and/or to transfer instructions and/or data to the network. Computer-readable storage mediums suitable for embodying computer program instructions and data include all forms of volatile and non-volatile memory, including by way of example semiconductor memory devices, e.g., DRAM, SRAM, EPROM, EEPROM, and flash memory devices; magnetic disks, e.g., internal hard disks or removable disks; magneto-optical disks; and optical disks, e.g., CD, DVD, HD-DVD, and Blu-ray disks. The processor and the memory can be supplemented by and/or incorporated in special purpose logic circuitry.

To provide for interaction with a user, the above described techniques can be implemented on a computing device in communication with a display device, e.g., a CRT (cathode ray tube), plasma, or LCD (liquid crystal display) monitor, a mobile device display or screen, a holographic device and/or projector, for displaying information to the user and a keyboard and a pointing device, e.g., a mouse, a trackball, a touchpad, or a motion sensor, by which the user can provide input to the computer (e.g., interact with a user interface element). Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, and/or tactile input.

The above described techniques can be implemented in a distributed computing system that includes a back-end component. The back-end component can, for example, be a data server, a middleware component, and/or an application server. The above described techniques can be implemented in a distributed computing system that includes a front-end component. The front-end component can, for example, be a client computer having a graphical user interface, a Web browser through which a user can interact with an example implementation, and/or other graphical user interfaces for a transmitting device. The above described techniques can be implemented in a distributed computing system that includes any combination of such back-end, middleware, or front-end components.

The components of the computing system can be interconnected by transmission medium, which can include any form or medium of digital or analog data communication (e.g., a communication network). Transmission medium can include one or more packet-based networks and/or one or more circuit-based networks in any configuration. Packet-based networks can include, for example, the Internet, a carrier internet protocol (IP) network (e.g., local area network (LAN), wide area network (WAN), campus area network (CAN), metropolitan area network (MAN), home area network (HAN)), a private IP network, an IP private branch exchange (IPBX), a wireless network (e.g., radio access network (RAN), Bluetooth, Wi-Fi, WiMAX, general packet radio service (GPRS) network, HiperLAN), and/or other packet-based networks. Circuit-based networks can include, for example, the public switched telephone network (PSTN), a legacy private branch exchange (PBX), a wireless network (e.g., RAN, code-division multiple access (CDMA) network, time division multiple access (TDMA) network, global system for mobile communications (GSM) network), and/or other circuit-based networks.

Information transfer over transmission medium can be based on one or more communication protocols. Communication protocols can include, for example, Ethernet protocol, Internet Protocol (IP), Voice over IP (VOIP), a Peer-to-Peer (P2P) protocol, Hypertext Transfer Protocol (HTTP), Session Initiation Protocol (SIP), H.323, Media Gateway Control Protocol (MGCP), Signaling System #7 (SS7), a Global System for Mobile Communications (GSM) protocol, a Push-to-Talk (PTT) protocol, a PTT over Cellular (POC) protocol, Universal Mobile Telecommunications System (UMTS), 3GPP Long Term Evolution (LTE) and/or other communication protocols.

Devices of the computing system can include, for example, a computer, a computer with a browser device, a telephone, an IP phone, a mobile device (e.g., cellular phone, personal digital assistant (PDA) device, smart phone, tablet, laptop computer, electronic mail device), and/or other communication devices. The browser device includes, for example, a computer (e.g., desktop computer and/or laptop computer) with a World Wide Web browser (e.g., Chrome™ from Google, Inc., Microsoft® Internet Explorer® available from Microsoft Corporation, and/or Mozilla® Firefox available from Mozilla Corporation). Mobile computing device include, for example, a Blackberry® from Research in Motion, an iPhone® from Apple Corporation, and/or an Android™-based device. IP phones include, for example, a Cisco® Unified IP Phone 7985G and/or a Cisco® Unified Wireless Phone 7920 available from Cisco Systems, Inc.

Comprise, include, and/or plural forms of each are open ended and include the listed parts and can include additional parts that are not listed. And/or is open ended and includes one or more of the listed parts and combinations of the listed parts.

One skilled in the art will realize the technology described herein may be embodied in other specific forms without departing from the spirit or essential characteristics thereof. The foregoing embodiments are therefore to be considered in all respects illustrative rather than limiting of the technology described herein.

What is claimed is:

1. A computerized method for secure validation of financial transactions, the method comprising:
   registering, by a server computing device, a mobile device to receive notification messages from the server computing device, wherein registering comprises:
   receiving, by the server computing device, a request to register the mobile device from a client computing device, the request including a first set of authentication credentials for a user of the client computing device;
   generating, by the server computing device, a user profile record based upon the first set of authentication credentials, the user profile record including a user identifier;

transmitting, by the server computing device, an application to the mobile device;

installing, by the mobile device, the application received from the server computing device;

generating, by the application on the mobile device, a device footprint for the mobile device comprising one or more data elements each containing values that in combination are unique to the mobile device;

establishing, by the mobile device, a first communication session with the server computing device;

transmitting, by the application on the mobile device, the device footprint and a second set of authentication credentials received from a user of the mobile device to the server computing device via the first communication session;

validating, by the server computing device, the second set of authentication credentials to determine an authenticated identity of the user of the mobile device;

generating, by the server computing device, a session record that includes a session identifier assigned to the first communication session and the authenticated identity of the user of the mobile device;

encrypting, by the server computing device, the session identifier into a secure credential;

generating, by the server computing device, an opaque token using carrier information in the device footprint;

transmitting, by the server computing device, the secure credential, the opaque token, and a contact address for a carrier associated with the mobile device to the mobile device via the first communication session;

establishing, by the mobile device, a communication session with a computing device at the carrier using the contact address for the carrier;

transmitting, by the application on the mobile device, the secure credential and the opaque token to the computing device at the carrier;

receiving, by the server computing device, carrier response data comprising the secure credential, the opaque token, and an identity of an owner of the mobile device;

matching, by the server computing device, the identity of the owner of the mobile device received in the carrier response data with the authenticated identity of the user;

generating, by the server computing device, a device record including a public device identifier used to index the device record;

generating, by the server computing device, a private device identifier; and storing, by the server computing device, the private device identifier and a phone number for the mobile device in the device record;

establishing, by the server computing device, a second communication session with the registered mobile device;

transmitting, by the server computing device, a notification message via the second communication session to a notification agent executing on the registered mobile device, wherein the message identifies activity associated with a financial account of a user of the registered mobile device;

receiving, by the server computing device, a response to the notification message via the first communication session from the application executing on the registered mobile device;

storing, by the server computing device, the response in a database coupled to the server computing device; and based upon the response, the server computing device either:
allowing the identified activity when the response is a first type;
denying the identified activity when the response is a second type; or
denying and reporting as fraud the identified activity when the response is a third type.

2. The method of claim 1, further comprising:

generating, by the mobile device, an encryption key pair comprising a public key and a private key;

storing, by the mobile device, the private key in an application-specific secure data store;

transmitting, by the mobile device, the public key to the server computing device;

storing, by the server computing device, the public key in the user profile record;

encrypting, by the server computing device, the user identifier, the public device identifier, and the private device identifier using the public key;

transmitting, by the server computing device, the encrypted user identifier, the encrypted public device identifier, and the encrypted private device identifier to the mobile device; and storing, by the mobile device, the encrypted user identifier, the encrypted public device identifier, and the encrypted private device identifier in the application-specific secure data store.

3. The method of claim 2, further comprising:

requesting, by the server computing device, registration approval from the mobile device;

receiving, by the server computing device, a response to the registration approval request from the mobile device; and registering, by the server computing device, the mobile device to receive subsequent notifications based upon the response to the registration approval request.

4. The method of claim 3, wherein requesting registration approval from the mobile device comprises:

transmitting, by the server computing device, an alert requesting registration approval to the notification agent of the mobile device via the second communication session;

launching, by the mobile device, the application in response to a user action based upon the alert;

transmitting, by the application on the mobile device, a request via the first communication session to the server computing device to display a registration approval notification message, the display request including the encrypted user identifier, the encrypted public device identifier, and the encrypted private device identifier;

validating, by the server computing device, the encrypted user identifier, the encrypted public device identifier, and the encrypted private device identifier against the user profile record and the device record;

transmitting, by the server computing device, the registration approval notification message via the first communication session to the mobile device for display.

5. The method of claim 1, further comprising verifying, by the server computing device, the device footprint received from the mobile device.

6. The method of claim 5, wherein verifying the device footprint comprises:
transmitting, by the server computing device, the device footprint to a computing device of a risk management service;
evaluating, by the risk management computing device, the device footprint to generate a risk score for the footprint; and
transmitting, by the risk management computing device, the risk score to the server computing device.

7. The method of claim 6, further comprising rejecting, by the server computing device, registration of the mobile device if the risk score meets or exceeds a predetermined threshold.

8. A system for secure validation of financial transactions, the system comprising a server computing device and a mobile device,
the mobile device comprising a processor and a memory storing instructions that, when executed by the processor, cause the processor to perform the steps of:
receiving an application from the server computing device;
installing the application received from the server computing device;
generating, by the application, a device footprint for the mobile device comprising one or more data elements each containing values that in combination are unique to the mobile device;
establishing a first communication session with the server computing device;
transmitting, by the application, the device footprint and a second set of authentication credentials received from a user of the mobile device to the server computing device via the first communication session;
receiving a secure credential, an opaque token, and a contact address for a carrier associated with the mobile device from the server computing device via the first communication session;
establishing a communication session with a computing device at the carrier using the contact address for the carrier;
transmitting, by the application, the secure credential and the opaque token to the computing device at the carrier;
the server computing device comprising a processor and a memory storing instructions that, when executed by the processor, cause the processor to perform the steps of:
registering the mobile device to receive notification messages from the server computing device, wherein registering comprises:
receiving a request to register the mobile device from a client computing device, the request including a first set of authentication credentials for the user of the client computing device;
generating a user profile record based upon the first set of authentication credentials, the user profile record including a user identifier;
transmitting the application to the mobile device;
validating the second set of authentication credentials to determine an authenticated identity of the user of the mobile device;
generating a session record that includes a session identifier assigned to the first communication session and the authenticated identity of the user of the mobile device;
encrypting the session identifier into the secure credential;
generating the opaque token using carrier information in the device footprint;
transmitting the secure credential, the opaque token, and the contact address for the carrier associated with the mobile device to the mobile device;
receiving carrier response data comprising the secure credential, the opaque token, and an identity of an owner of the mobile device from the computing device at the carrier;
matching the identity of the owner of the mobile device received in the carrier response data with the authenticated identity of the user;
generating a device record including a public device identifier used to index the device record;
generating a private device identifier;
storing the private device identifier and a phone number for the mobile device in the device record;
establishing a second communication session with the registered mobile device;
transmitting a notification message via the second communication session to a notification agent executing on the registered mobile device, wherein the message identifies activity associated with a financial account of a user of the registered mobile device;
receiving a response to the notification message via the first communication session from the application executing on the registered mobile device;
storing the response in a database coupled to the server computing device; and
based upon the response, the server computing device either:
allowing the identified activity when the response is a first type;
denying the identified activity when the response is a second type; or
denying and reporting as fraud the identified activity when the response is a third type.

9. The system of claim 8, wherein, when executed by the processor of the server computing device, the instructions stored in the memory of the server computing device cause the processor to perform the step of:
receiving, from the mobile device, a public key of an encryption key pair generated by the mobile device;
and wherein, when executed by the processor of the mobile device, the instructions stored in the memory of the mobile device cause the processor to perform the steps of:
generating the encryption key pair comprising a public key and a private key;
storing the private key in an application-specific secure data store;
storing the public key in the user profile record;
encrypting the user identifier, the public device identifier, and the private device identifier using the public key; and
transmitting the encrypted user identifier, the encrypted public device identifier, and the encrypted private device identifier to the mobile device for storage in the application-specific secure data store.

10. The system of claim 9, wherein, when executed by the processor of the server computing device, the instructions stored in the memory of the server computing device cause the processor to perform the steps of:
- requesting registration approval from the mobile device;
- receiving a response to the registration approval request from the mobile device; and
- registering the mobile device to receive subsequent notifications based upon the response to the registration approval request.

11. The system of claim 10, wherein requesting registration approval from the mobile device comprises:
- transmitting an alert requesting registration approval to the notification agent of the mobile device via the second communication session;
- receiving, from the application on the mobile device, a request via the first communication session to display a registration approval notification message, the display request including the encrypted user identifier, the encrypted public device identifier, and the encrypted private device identifier;
- validating the encrypted user identifier, the encrypted public device identifier, and the encrypted private device identifier against the user profile record and the device record; and
- transmitting the registration approval notification message via the first communication session to the mobile device for display.

12. The system of claim 8, wherein, when executed by the processor of the server computing device, the instructions stored in the memory of the server computing device cause the processor to perform the step of verifying the device footprint received from the mobile device.

13. The system of claim 12, wherein verifying the device footprint comprises:
- transmitting the device footprint to a computing device of a risk management service configured to evaluate the device footprint and to generate a risk score for the footprint; and
- receiving the risk score from the risk management computing device.

14. The system of claim 13, wherein, when executed by the processor of the server computing device, the instructions stored in the memory of the server computing device cause the processor to perform the step of rejecting registration of the mobile device if the risk score meets or exceeds a predetermined threshold.

* * * * *